United States Patent [19]

Hachmeister et al.

[11] 4,415,577
[45] Nov. 15, 1983

[54] BIS-SPARTEINE DERIVATIVES AND METHOD OF USING SAME IN THERAPY

[75] Inventors: Bernd Hachmeister; Wolfgang Kehrbach; Ulrich Kuehl; Gerd Buschmann, all of Hanover, Fed. Rep. of Germany

[73] Assignee: Kali-Chemie Pharma GmbH, Hanover, Fed. Rep. of Germany

[21] Appl. No.: 294,207

[22] Filed: Aug. 19, 1981

[30] Foreign Application Priority Data

Aug. 27, 1980 [DE] Fed. Rep. of Germany ....... 3032219

[51] Int. Cl.$^3$ .................. A61K 31/435; C07D 471/22
[52] U.S. Cl. ...................................... 424/258; 546/71
[58] Field of Search ........................... 546/71; 424/258

[56] References Cited

FOREIGN PATENT DOCUMENTS 25069 9/1979 European Pat. Off. .
2360475 6/1975 Fed. Rep. of Germany .

OTHER PUBLICATIONS

Vinogradov et al., *Chemical Abstracts,* vol. 77, 1972, Abst. #58768n.
Herlem et al., *Tetrahedron,* vol. 29, pp. 2195 to 2202, 1973.

*Primary Examiner*—Nicholas S. Rizzo
*Assistant Examiner*—D. B. Springer
*Attorney, Agent, or Firm*—Schwartz, Jeffery, Schwaab, Mack, Blumenthal & Koch

[57] ABSTRACT

Disclosed are a novel dimeric sparteine derivative, the 17S,17'S-bissparteine, and its physiologically compatible acid addition salts. Said compounds are produced by dimerization of 17-hydroxy sparteine or 17-dehydrosparteine salts by means of activated magnesium or an alkali metal. Pharmaceutical compositions containing said novel dimeric sparteine derivatives and their preparation are also described.

5 Claims, No Drawings

BIS-SPARTEINE DERIVATIVES AND METHOD OF USING SAME IN THERAPY

BACKGROUND OF THE INVENTION

1. Field of the Invention

The present invention relates to a novel and highly advantageous sparteine derivative and more particularly to 17S,17'S-bissparteine, to a process of producing said compound, to pharmaceutical compositions containing same, and to a method of using said compositions in the treatment of arrhythmias.

2. The Prior Art

It is known that sparteine and the 17-alkyl derivatives of sparteine are characterized and distinguished by their valuable pharmacological properties and more particularly by their anti-arrhythmic activity (German Published Application No. 23 60 475; European Patent Application No. 79 103 315.2).

It has proved to be of advantage that an anti-arrhythmic drug exhibits a considerable therapeutic range of activity, i.e. that its therapeutic index or the ratio between its toxic dose and its therapeutically effective dose is as great as possible. Furthermore, it is also advantageous if an anti-arrhythmic drug exerts its activity for a prolonged period of time even on peroral administration.

The known sparteine compounds, however, have the disadvantage that they have only a relatively low anti-arrhythmic activity or that their anti-arrhythmic effect is only of short duration when they are administered perorally. Thus there is a great demand for anti-arrhythmic agents having the basic sparteine ring structure, but with considerably improved pharmacological properties.

SUMMARY OF THE INVENTION

It is one object of the present invention to provide a novel and highly effective compound with the basic sparteine structure which, in contrast to known sparteine compounds, has a high and prolonged anti-arrhythmic activity and a therapeutic index superior to that of the known sparteine compounds. Another object of the present invention is to provide a novel and advantageous process of making such a highly effective sparteine derivative.

Still another object of the present invention is to provide advantageous and highly effective pharmaceutical compositions containing such a highly effective anti-arrhythmic sparteine derivative which exhibits a prolonged anti-arrhythmic effect even on peroral administration.

A further object of the present invention is to provide a method of using such a novel and highly effective sparteine derivative in the treatment of anti-arrhythmias.

Other objects of the present invention and advantageous features thereof will become apparent as the description proceeds.

In principle the present invention solves the problem of providing a highly effective anti-arrhythmic sparteine derivative by producing 17S,17'S-bissparteine of the following formula:

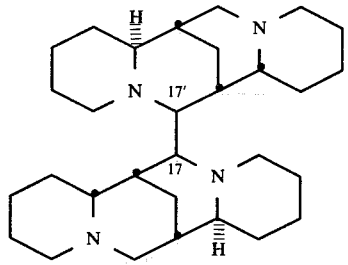

and its physiologically compatible acid addition salts and using said compounds as anti-arrhythmic agents in therapy.

A number of different dimeric sparteines hve been described in the literature (H.-G. Boit "Ergebuisse der Alkaloid-Chemie bis 1960", [Achievements in Alkaloid Chemistry Up To 1960], page 197, published by Akademie-Verlag, Berling 1961; R. H. F. Manske "The Aklaloids" Volume IX, page 194, published by Academic Press, New York 1967).

These known $\alpha$-, $\beta$-, $\gamma$-, or, respectively, $\delta$-diplospartyrines are compounds with chemical linkages or bonds between the carbon atom 17, on the one hand, and the carbon atoms 5', 12', or, respectively, 14'. There are described, however, no compounds of the 17S,17'S-bissparteine type as they are produced according to the present invention. Said 17S,17'S-bissparteine compound is a novel compound.

Said novel dimeric 17S,17'S-bissparteine according to the present invention can be produced by reacting 17-hydroxy sparteine or a salt of 17-dehydrosparteine, preferably the perchlorate, with an alkali metal or with activated magnesium in a suitable solvent.

The resulting compound can be converted, if desired, into its acid addition salts by reaction with physiologically compatible acids.

Suitable solvents to be used in the preparation of said bissparteine compounds are preferably aprotic solvents. Ethers and especially tetrahydrofuran, diethyl ether, ethylene glycol dimethyl ether, and mixtures thereof have proved to be especially useful aprotic solvents.

Preferably the reaction is carried out at the boiling temperature of the solvent. When using solvents of a higher boiling point than that of diethyl ether, the reaction mixture may also be heated to a temperature below the boiling point of the respective solvent.

Magnesium having an active surface can be produced by various processes:

(a) By amalgamation with a mercury salt, for instance, by reaction of metallic magnesium with mercury $(II)$ chloride.

(b) By reaction of metallic magnesium with a catalytically effective amount of an organic monohalogeno compound, for instance, with bromo veratrole and methyl iodide.

(c) By precipitation of finely divided magnesium from an anhydrous magnesium salt by means of a less noble metal, for instance, by means of metallic sodium or potassium.

(d) By treatment of metallic magnesium with a proton donor. According to a specific variant of said treatment there is used an acid as proton donor.

When proceeding according to this last mentioned activation method, the metallic magnesium is activated in the presence of the sparteine compound used as starting material and more particularly in the presence of 17-hydroxy sparteine. Although the dimerization to the bissparteine can also be carried out in a protic solvent in the presence of a proton donor, for instance, in the system water/hydrogen halide, it is of advantage to use, as solvent, a mixture of proton donor and an aprotic solvent. The amount of proton donor in said mixture, calculated with respect to the total volume of the liquid phase, is between about 0.5% by volume and about 50% by volume and preferably between about 1% by volume and about 30% by volume. When employing an acid as proton donor, it is preferred to use an organic acid and more particularly acetic acid or trifluoro acetic acid. When the reaction is carried out with an alkali metal, there is used preferably a finely divided alkali metal and more particularly finely divided sodium.

Isolation and recovery of the 17S,17'S-bissparteine base from the reaction mixture and its purification are effected in a manner and by methods known per se. More particularly the bissparteine compound can be isolated from its alkaline reaction mixture by extraction and the resulting crude product can be purified by chromatography and/or by recrystallization, or mixtures thereof.

The acid addition salts of 17S,17'S-bissparteine are obtained according to the present invention by reaction of the basic bissparteine compound with acids which are capable of forming physiologically innocuous acid addition salts. As examples of such salts there may be mentioned the halogenides and more particularly the hydrochloride, fumarate, naphthalene sulfonate, sulfate, phosphate, maleinate, citrate, or tartrate.

The acid addition salts of 17S,17'S-bissparteine obtained according to the process of the present invention are stable in aqueous solution as well as in solid form and can be stored for a prolonged period of time. They can be compounded to medicines and drugs by mixing them with conventional pharmaceutical carrier substances and/or excipients.

The novel 17S,17'S-bissparteine according to the present invention exhibits more favorable pharmacological, in particular more favorable antiarrhythmic properties than sparteine or known 17-alkylsparteines. Thus the novel dimer sparteine derivative has a similar influence as that of the known sparteines on the functional refractory period yet at considerably lower dosages, whereby toxicity of the novel compound is similar or less than that of known sparteine derivatives.

Furthermore, after oral application, the novel compound of the present invention retains its good effect even after a period of 3 hours. Contrary to this, when known spartein compounds are tested under the same conditions no effect can be detected anymore after such a period.

The superior properties of the compound according to the present invention as compared with sparteine and a representative 17-alkylsparteine can be seen from the data in table 1 below.

The following data are given in the table.

The acute toxicity of the compounds is determined in male NMRI-mice (body weight range 18–22 g) after oral (p.o) administration. The $LD_{50}$ is defined as that dose in $\mu mol/kg$ which causes a 50% mortality rate of the test animals on the 7th day after application. The calculation of the $LD_{50}$ is carried out by probitanalysis (see L. Cavalli-Sforza, Grundbegriffe der Biometric, Gustav Fischer Verlag Stuttgart (1964).

The influence of the novel compound on aconitin-induced arrhythmic effects is determined on male Wistar rats (weighing 280–350 g) which are treated with an aconitin infusion according to the method of Raschak (M. Raschak, Arzneim. Forschung (Drug Research) 25 (1975) pp. 639–641). The effective dose which is given in $\mu mol/kg$, is the dose which cause a significant difference in time between the starting of the aconitin-induced arrhythmic effect in animals treated with the active ingredient and the starting of this aconitin-induced effect in an untreated control group of animals. In order to be considered effective the dose must cause a significant prolongation of the period until the aconitin-induced arrhythmic effects start, and it must be effective against at least two of the aconitin-induced arrhythmic symptoms (extrasystoles, ventricular flutter, ventricular tachycardia). The test compound is applied orally inform of a 2% suspension of tylose $^R$ MH 50 three hours before the aconitin-infusion is started.

As a standard dose one tenth of the $LD_{50}$ in mice is used. If a test compound is effective at this dose, the dose is reduced in a following test. The statistical t-test method according to Student using logarithmic values of the effective values is used for significance testing (see Lothar Sachs, Statistische Auswertungsmethoden, Springer Verlag 1969).

The prolongation of the functional refractory period (FRP) in the isolated left atria of female guinea pigs (albino-pirbright-white guinea pigs, body weight range 300–400 g) is determined according to the double stimulus method of Govier (see W. C. Govier, *J. Pharmakol. Exp. Ther.* 148 (1965) pp. 100–105). The concentrations which are given in the table below are the concentrations in $\mu mol/l$ are those which 18 minutes after application cause a prolongation of the functional refractory period to 125%.

Since some of the data are given in $\mu mol/kg$ and $\mu mol/l$ respectively, the calculated molecular weight (MW) of the test compounds is also given in the table below.

The novel 17S,17'S-bissparteine according to the present invention, exhibits valuable pharmacological properties and, therefore, is useful in medical treatment. In particular, it is useful in the treatment and prophylaxis of diseases of the coronary and circularly system, e.g. they are useful as antiarrhythmics in the treatment of heart rhythm disorders, since they exhibit antiarrhythmic activities, as is indicated in standard tests, e.g. measurement of the functional refractory period in the isolated left atria of a guinea pig.

For the above-mentioned uses, the administered 25 doses can vary considerably depending on the type of the compound, the animal, the mode of administration, the treated conditions and the therapy which is desired. Usually satisfactory results are obtained with dosages between 0,05 and 25 mg=kg body weight. These doses can be administered enterally, preferably orally, or parenterally. For example, daily oral doses for larger mammals can be chosen between 0,5 and 100 mg.

| Tested active compound | Mol. Weight (g./mole) | $LD_{50}$ $\mu mole/kg.$ per os | Aconitine test, effective dose $\mu mole/kg.$ per os | FRP 125% $\mu mole/l.$ |
|---|---|---|---|---|
| Sparteine sulfate | 423 | 540 | >54 | 34 |
| Pentyl sparteine | 695 | 1800 | >180 | 9 |

-continued

| Tested active compound | Mol. Weight (g./mole) | LD$_{50}$ μmole/kg. per os | Aconitine test, effective dose μmole/kg. per os | FRP 125% μmole/l. |
|---|---|---|---|---|
| tartrate Salt of 17S,17'S—bissparteine with 2 moles of L(+)-tartaric acid | 767 | >1900 | 33 | 5 |

This Table shows that the 17S,17'S-bissparteine according to the present invention is not only less toxic, but also more effective than the known tested sparteine compounds.

DESCRIPTION OF THE PREFERRED EMBODIMENTS

The following examples serve to illustrate the present invention without, however, limiting the same thereto.

The starting materials are prepared as follows:

17-Hydroxy sparteine is produced from sparteine as described in German Published Application No. 28 25 117.4.

17-Dehydrosparteine perchlorate is obtained from 17-hydroxy sparteine by proceeding as described by M. Rink and K. Grabowski in "*Arch.Pharm.*" Vol. 289 (1956), page 695.

EXAMPLE 1

Dimerization of 17-dehydrosparteine perchlorate by means of freshly precipitated, finely divided magnesium, thereby using potassium as activating agent 4 g. of anhydrous magnesium chloride are heated to boiling under reflux with 1.5 g. of metallic potassium in 100 ml. of absolute tetrahydrofurane for 3½ hours, while stirring. As a result thereof metallic magnesium is precipitated in the form of a black dispersion in the tetrahydrofurane. 12 g. of 17-dehydrosparteine perchlorate are added to the resulting suspension after it has been cooled to room temperature. The mixture is heated to boiling for 2½ hours, while stirring vigorously. Thereupon 10 ml. of isopropanol are added to the reaction mixture while heating is continued. The suspension is then cooled and acidified by the addition of dilute hydrochloric acid. After the entire magnesium which has been used in excess of the required amount, has been dissolved, the mixture is extracted twice, each time with 100 ml. of methylene chloride. 20 g. of ammonium chloride are added to the aqueous phase and the mixture is rendered alkaline by the addition of a 20% sodium hydroxide solution. The resulting alkaline mixture is then extracted twice, each time with 100 ml. of diethyl ether. The separated organic phase is concentrated by evaporation in the vacuum of a water-jet pump and the residue is dissolved in methylene chloride. After drying the resulting solution over magnesium sulfate, the solvent is distilled off in a vacuum. After chromatographically purifying the resulting compound over a column of aluminum oxide of the degree of activity II-III, by elution with a mixture of hexane and diethyl ether in the proportion of 90:10, there are isolated 6.2 g. of pure, crystalline 17S,17'S-bissparteine.

Yield: 73.8% of the theoretical yield. Melting point: 178° C. $\alpha_D^{20}$: −101.4° in methylene dichloride.

A crystalline ditartrate salt with the melting point of 186° C. is obtained by the addition of the calculated amount of L(+)-tartaric acid to a hot solution of the bissparteine base in isopropanol.

The amorphous tetrahydrochloride salt can be produced in an analogous manner by adding an excess of an ethanolic hydrochloric acid solution to a solution of the bissparteine base in isopropanol and evaporating the reaction mixture to dryness.

EXAMPLE 2

Dimerization of 17-hydroxy sparteine by means of freshly precipitated, finely divided magnesium activated by using metallic potassium The reaction is carried out by proceeding in an analogous manner as described in Example 1. In place of 12 g. of 17-dehydrosparteine perchlorate there are reacted 5 g. of 17-hydroxy sparteine. After purification of the reaction product by means of column chromatography, there are obtained 2.4 g. of 17S,17'S-bissparteine corresponding to a yield of 51.4% of the theoretical yield.

EXAMPLE 3

Dimerization of 17-dehydrosparteine perchlorate by means of freshly precipitated, finely divided magnesium activated by using metallic sodium as activating agent The reaction is carried out in an analogous manner as described in Example 1; but in contrast thereto the magnesium is not activated by means of metallic potassium but is precipitated by means of a 30% dispersion of metallic sodium in toluene. When proceeding in this manner, the dimeric compound is obtained after purification as described in Example 1, in a yield of 49.5% of the theoretical yield.

EXAMPLE 4

Dimerization of 17-hydroxy sparteine by means of amalgamated magnesium 2.4 g. of magnesium chips are pretreated with 7 g. of mercuric chloride in 150 ml. of boiling tetrahydrofurane for 2 hours. A solution of 10 g. of 17-hydroxy sparteine in 100 ml. of tetrahydrofurane is added drop by drop to the resulting activated magnesium suspension. Heating to boiling under reflux is continued for 2½ hours. The resulting reaction solution is then worked up in the manner described in Example 1. 4.6 g. of 17S,17'S-bissparteine, corresponding to a yield of 49.3% of the theoretical yield, are obtained.

EXAMPLE 5

Dimerization of 17-dehydrosparteine perchlorate by means of amalgamated magnesium 10 g. of 17-dehydrosparteine perchlorate in 75 ml. of tetrahydrofurane are reacted with amalgamated magnesium under the conditions as described in Example 4. The amalgamated magnesium was obtained by a treatment of 1.45 g. of magnesium chips with 3.25 g. of mercuric chloride. The crude reaction product isolated after the acid-base separation step, as described in Example 1, is purified by crystallization—and not by subjecting it to column chromatography. For this purpose the crude product is dissolved in boiling dichloro methane. On adding acetone to the resulting solution, 17S,17'S-bissparteine precipitates.

Yield: 6.14 g. corresponding to 87.4% of the theoretical yield.

EXAMPLE 6

Dimerization of 17-dehydrosparteine perchlorate by means of magnesium with the addition of organic monohalogeno compounds A solution of 0.3 ml. of methyl iodide in 25 ml. of diethyl ether is added drop by drop to 3.3 g. of magnesium chips. The mixture is boiled under reflux for 10 minutes. Thereupon 29.5 g. of bromo veratrol in 25 ml. of diethyl ether are added. Boiling under reflux of the resulting reaction mixture is continued for 2 more hours. A suspension of 15 g. of 17-dehydrosparteine perchlorate in 30 ml. of tetrahydrofurane is then added thereto and boiling of the reaction mixture under reflux is continued for 4 more hours. Working up of the reaction mixture and purification of the reaction product are carried out as described in Example 1. 3.2 g. of the dimeric compound, corresponding to a yield of 30.5% of the theoretical yield, are obtained.

EXAMPLE 7

Dimerization of 17-dehydrosparteine perchlorate by means of finely divided metallic sodium 10 g. of 17-dehydrosparteine perchlorate and 1.7 g. of a 40% dispersion of metallic sodium of the particle size of 10μ in paraffin are heated to boiling in 300 ml. of tetrahydrofurane for 8 hours. After the addition of 10 ml. of isopropanol, the reaction mixture is hydrolyzed by the addition of dilute hydrochloric acid. The precipitated paraffin is filtered off by suction and the aqueous filtrate is worked up in an analogous manner as described in Example 1. 4.55 g. of 17S,17'S-bissparteine, corresponding to a yield of 65% of the theoretical yield, are obtained.

EXAMPLE 8

Dimerization of 17-hydroxy sparteine by means of magnesium and a proton donor 7.8 g. of 17-hydroxy sparteine are dissolved in a mixture of 7.8 ml. of glacial acetic acid and 39 ml. of tetrahydrofurane. 0.76 g. of magnesium are added to the solution and the resulting reaction mixture is heated to boiling under reflux for 2 hours.

WORKING UP OF THE RESULTING REACTION MIXTURE

Variant A:

The reaction mixture is concentrated by evaporation and the residue is dissolved in an aqueous 20% ammonium chloride solution. The resulting solution is then adjusted to pH of 9.0 by the addition of a concentrated aqueous ammonia solution. The alkaline solution is then extracted three times with methylene chloride.

Yield of crude reaction product: 5.6 g.

Variant B:

The reaction mixture is diluted to a volume of 100 ml. by the addition of tetrahydrofurane. Gaseous ammonia is introduced so as to adjust the pH-value of the solution to a pH of 11.10. After addition of 240 ml. of diethyl ether, the precipitate is filtered off by suction. The filtrate is dried and concentrated by evaporation.

Yield of crude reaction product: 6.2 g.

PURIFICATION OF THE CRUDE REACTION PRODUCT 10.7 g. of the crude compound are chromatographically purified on 230 g. of alumina by using cyclohexane as eluting agent.

Yield: 7.8 g.

The 17S,17'S-bissparteine is obtained in crystalline form by recrystallization from a mixture of methylene chloride and acetone and also by recrystallization from ethanol.

EXAMPLE 9

Dimerization of 17-hydroxy sparteine by means of magnesium in the presence of a proton donor 2.1 g. of 17-hydroxy sparteine are dissolved in a mixture of 1 ml. of trifluoro acetic acid and 30 ml. of tetrahydrofurane. After addition of 0.4 g. of magnesium the reaction mixture is heated to boiling under reflux for 3 hours. The resulting reaction mixture is worked up as described hereinabove in Example 8, Variant A.

Yield of crude reaction product: 1.5 g.

EXAMPLE 10

Dimerization of 17-hydroxy sparteine by means of magnesium in the presence of a proton donor 1.4 g. of 17-hydroxy sparteine are dissolved in a mixture of 1.4 ml. of acetic acid and 10 ml. of ethylene glycol dimethyl ether. 0.13 g. of magnesium are added to the resulting solution which is then heated to boiling under reflux for 2 hours. The reaction mixture is worked up as described hereinabove in Example 8, Variant A.

Yield of crude reaction product: 1.0 g.

The following Examples 11 to 14 describe processes of producing pharmaceutical compositions containing pharmacologically effective 17S,17'S-bissparteine compounds according to the present invention without, however, being limited thereto.

EXAMPLE 11

Tablets

Composition:

| | |
|---|---|
| 17S,17'S—bissparteine ditartrate | 20.0 mg. |
| Lactose | 40.0 mg. |
| Corn starch | 30.0 mg. |
| "Kollidon 25"* | 5.0 mg. |
| "Aerosil 200"** | 0.2 mg. |
| Stearic acid | 3.0 mg. |
| Total amount in one tablet: | 98.2 mg. |

*"Kollidon" TM: Binding agent, polyvinyl pyrrolidone.
**"Aerosil" TM: Finely divided silicon dioxide.

Manufacture of tablets:

17S,17'S-bissparteine ditartrate, lactose, and corn 17S,17'S-Bissparteine ditartrate, lactose, and corn starch are premixed in a mixing device of the "Diosna" type. The resulting premixture is thoroughly moistened by means of an aqueous solution of "Kollidon 25". The resulting granulate, which is still moist, is passed through a 1.5 mm. sieve. After drying, the sieved material is passed through a 1.0 mm. sieve and mixed with the "Aerosil 200" and the stearic acid. The resulting mixture, which is ready for molding, is compressed to tablets on a turntable tabletting machine. Each tablet weights, as an average, 98.2 mg. and contains 20 mg. of 17S,17'S-bissparteine ditartrate.

EXAMPLE 12

Capsules

Composition:

| 17S,17'S—bissparteine ditartrate | 20.0 mg. |
|---|---|
| Spray-dried lactose | 50.0 mg. |
| Corn starch | 25.0 mg. |
| "Aerosil 200"** | 0.5 mg. |
| Magnesium stearate | 1.5 mg. |
| Total amount of one capsule: | 97.0 mg. |

Manufacture of capsules:

17S,17'S-bissparteine ditartrate, lactose, and corn starch are mixed in a "Kubus" mixing device for 20 minutes. "Aerosil 200" and magnesium stearate are passed through an 0.2 mm. sieve and are then added to the premixture. The resulting mixture is then thoroughly mixed for 5 minutes. The powder mixture thus obtained is then filled into capsules of size 4 by means of a capsule filling machine. Each capsule contains, as an average, 97 mg. of the above given powder mixture corresponding to 20 mg. of 17S,17'S-bissparteine ditartrate.

EXAMPLE 13

Ampoules

Composition:

| 17S,17'S—bissparteine tetrahydrochloride | 5.0 mg. |
|---|---|
| Sodium chloride | 9.0 mg. |
| Bidistilled water | ad 1.0 ml. |

Manufacture of ampoules:

17S,17'S-bissparteine tetrahydrochloride and sodium chloride are dissolved in bidistilled water. The resulting solution is filtered, filled into ampoules, and, after sealing the ampoules, sterilized at 120° C. for 20 minutes. Each ampoule contains 1 ml. of the above given solution corresponding to 5 mg. of 17S,17'S-bissparteine tetrahydrochloride.

EXAMPLE 14

Pellets

Commercially available sugar pellets of a diameter of about 3 mm. are sprayed with an aqueous solution of 17S,17'S-bissparteine ditartrate in a rotating vessel. The thus impregnated pellets are then dried. Each pellet contains about 1 mg. of the active compound.

Of course, many changes and variations in the process of producing 17S,17'S-bissparteine and its acid addition salts, in the reaction conditions, temperatures, and duration, in the activation of the magnesium, the solvents and proton donors used, the manner of working up the dimerization mixture and of purifying the dimeric 17S,17'S-bissparteine, in the production of physiologically compatible acid addition salts of said compound, in the preparation of pharmaceutical compositions useful in therapy, and the like may be made by those skilled in the art in accordance with the principles set forth herein and in the claims annexed hereto.

What is claimed is:

1. A dimeric sparteine derivative selected from the group consisting of 17S,17'S-bissparteine of the Formula

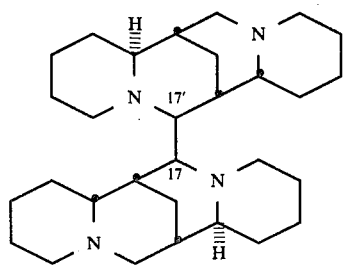

and its physiologically compatible acid addition salts.

2. The acid addition salt of 17S,17'S-bissparteine according to claim 1 with 2 moles of L(+)-tartaric acid, said salt being the 17S,17'S-bissparteine ditartrate.

3. The acid addition salt of 17S,17'S-bissparteine according to claim 1 with 4 moles of hydrochloric acid, said salt being 17S,17'S-bissparteine tetrahydrochloride.

4. A pharmaceutical composition having anti-arrhythmic activity, said composition comprising, as anti-arrhythmic agent, a 17S,17'S-bissparteine compound selected from the group consisting of 17S,17'S-bissparteine and its physiologically compatible acid addition salts, and a pharmaceutical excipient.

5. In a method of treating arrhythmias, the step which comprises administering to a human patient suffering from arrhythmias an anti-arrhythmias effective amount of a pharmaceutical composition according to claim 4.

* * * * *